(12) United States Patent
Wang et al.

(10) Patent No.: US 11,027,140 B2
(45) Date of Patent: Jun. 8, 2021

(54) SELF-POWERED, AUTO-RESPONSIVE IMPLANTED VAGAL NERVE STIMULATOR FOR WEIGHT CONTROL

(71) Applicant: Wisconsin Alumni Research Foundation, Madison, WI (US)

(72) Inventors: Xudong Wang, Middleton, WI (US); Weibo Cai, Madison, WI (US); Guang Yao, Chengdu (CN); Lei Kang, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 117 days.

(21) Appl. No.: 16/009,553

(22) Filed: Jun. 15, 2018

(65) Prior Publication Data
US 2019/0381324 A1    Dec. 19, 2019

(51) Int. Cl.
*A61N 1/36* (2006.01)
*A61N 1/378* (2006.01)

(52) U.S. Cl.
CPC ....... *A61N 1/3785* (2013.01); *A61N 1/36007* (2013.01); *A61N 1/36053* (2013.01); *A61N 1/36085* (2013.01)

(58) Field of Classification Search
CPC .............. A61N 1/3785; A61N 1/36007; A61N 1/36053; A61N 1/36085
See application file for complete search history.

(56) References Cited

U.S. PATENT DOCUMENTS

| | | | | |
|---|---|---|---|---|
| 2008/0284599 A1* | 11/2008 | Zdeblick | ............... | A61B 5/1473 340/572.1 |
| 2010/0114142 A1* | 5/2010 | Albrecht | ................. | A61F 5/004 606/191 |
| 2014/0243848 A1* | 8/2014 | Auricchio | .......... | A61N 1/37205 606/129 |
| 2014/0277249 A1* | 9/2014 | Connor | ................. | A61F 5/0026 607/40 |
| 2014/0338458 A1* | 11/2014 | Wang | ..................... | G01H 11/06 73/658 |
| 2016/0156282 A1* | 6/2016 | Kim | ..................... | A61N 1/3787 607/61 |

(Continued)

OTHER PUBLICATIONS

Pang et al., "An Alginate Film-Based Degradable Triboelectric Nanogenerator", The Royal Society of Chemistry 2018, 6719-6726, Feb. 12, 2018.

(Continued)

*Primary Examiner* — Eric D. Bertram
(74) *Attorney, Agent, or Firm* — Boyle Fredrickson S.C.

(57) ABSTRACT

The invention provides an implantable vagal nerve stimulator having a "passive" generating power source that harvests the stomach's movements to transform kinetic energy to electrical charge without the need for a battery. In this regard, the invention is self-powering and is automatically timed to stomach peristalsis. While sporadic stimulation to the vagal nerve would seem too infrequent to cause weight loss effects, electrical stimulation delivered at the optimal time (e.g., during food consumption) has been found to optimize the effects of vagal nerve stimulation, giving the user's brain a "full stomach" signal before the user overconsumes food.

20 Claims, 4 Drawing Sheets

(56) References Cited

U.S. PATENT DOCUMENTS

| | | | |
|---|---|---|---|
| 2016/0184595 A1* | 6/2016 | Hossainy | A61N 1/3756 604/288.04 |
| 2017/0119235 A1* | 5/2017 | Hyde | A61B 1/00108 |
| 2018/0168801 A1* | 6/2018 | Kim | A61N 1/3606 |
| 2019/0261920 A1* | 8/2019 | Euliano | A61B 5/065 |
| 2019/0321612 A1* | 10/2019 | Cinquin | A61M 31/002 |

OTHER PUBLICATIONS

Laskiewicz et al., "Capsaicin Induced Deafferentation Enhances the Effect of Electrical Vagal Nerve Stimulation of Food Intake and Body Mass", Journal of Physiology and Pharmacology 2004, 55, 1, 155-163.

Bugajski, et al., "Effect of Long-Term Vagal Stimulation on Food Intake and Body Weight During Diet Induced Obesity in Rats", Journal of Physiology and Pharmacology 2007, 58, Suppl 1, 5-12, Apr. 2007.

Ikramuddin et al., "Effect of Reversible Intermittent Intra-abdominal Vagal Nerve Blockade on Morbid Obesity", Jama, vol. 312, No. 9, 915-922, Sep. 3, 2014.

Krolczyk et al., "Effects of Continuous Microchip (MC) Vagal Neuromodulation on Gastro Intestinal Function in Rats", Journal of Physiology and Pharmacology 2001, 52, 4, 705-715, Dec. 2001.

Camilleri et al., "Intra-abdominal Vagal Blocking (VBLOC Therapy): Clinical Results with a New Implantable Medical Device", Surgery, vol. 143, No. 6, 723-731, Jun. 2008.

Ziomber et al., "Magnetically Induced Vagus Nerve Stimulation and Feeding Behavior in Rats", Journal of Physiology and Pharmacology 2009, 60, 3, 71-77, Sep. 2009.

Williams et al., "Vagotomy Dissociates Short- and Long-Term Controls of Circulating Ghrelin", Endocrinology 144(12): 5184-5187, Dec. 2003.

Krolczyk et al., "The Effects of Baclofen on the Feeding Behaviour and Body Weight of Vagally Stimulated Rats", Journal of Physiology and Pharmacology 2005, 56, 1, 121-131, Mar. 2005.

Apovian et al. "Two-Year Outcomes of Vagal Nerve Blocking (vBloc) for the Treatment of Obesity in the ReCharge Trial", Obes Surg (2017) 27: 169-176, Aug. 10, 2016.

Hwang et al., "Update on Bariatric Surgical Procedures and an Introduction to the Implantable Weight Loss Device: the Maestro Rechargeable System", Medical Devices: Evidence and Research 2016:9 291-299, Aug. 17, 2016.

* cited by examiner

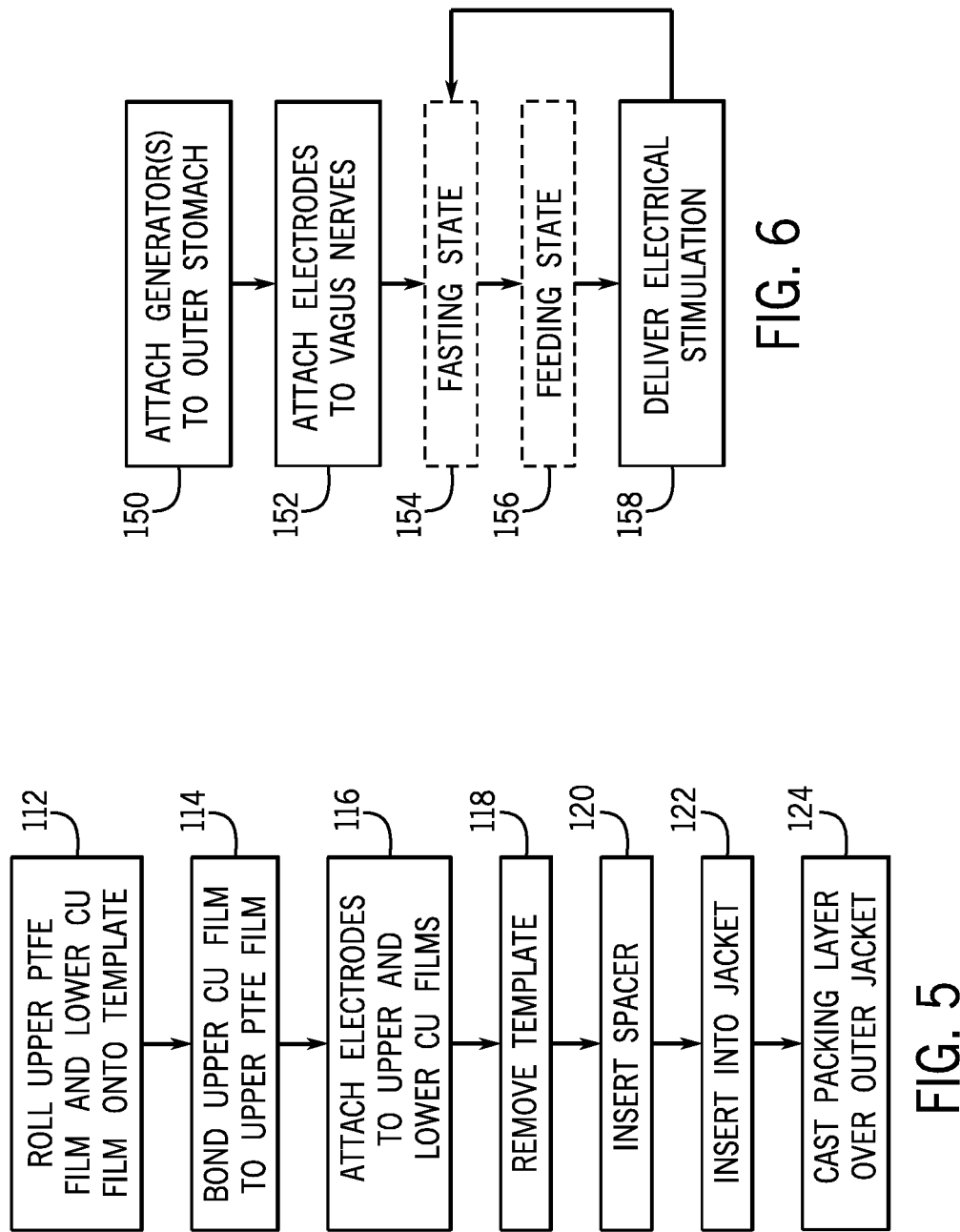

SELF-POWERED, AUTO-RESPONSIVE IMPLANTED VAGAL NERVE STIMULATOR FOR WEIGHT CONTROL

STATEMENT REGARDING FEDERALLY SPONSORED RESEARCH OR DEVELOPMENT

This invention was made with government support under EB021336 awarded by the National Institutes of Health. The government has certain rights in the invention.

CROSS REFERENCE TO RELATED APPLICATION

—

BACKGROUND OF THE INVENTION

The present invention relates to a method and apparatus for weight control, and more particularly, an improved vagal nerve stimulation device for weight control.

Obesity is a risk factor for numerous chronic diseases, including cardiovascular disease, diabetes mellitus, chronic kidney disease, cancers, and musculoskeletal disorders. Approaches to treat obesity include both non-surgical and surgical treatments, however, existing approaches have had varying degrees of success. For example, non-surgical treatments such as physical exercise and weight loss drugs have high occurrence of rebound or risk of side effects while surgical treatments such as gastric bypass, biliopancreatic diversion, and sleeve gastrectomy have shown efficacious results but are highly invasive procedures with the potential of serious complications.

The vagus (tenth cranial) nerve is a mixed parasympathetic nerve containing both afferent (arriving in the brain) and efferent (exiting the brain) sensory fibers, acting as a signal bridge to transport information between the brain, i.e., the center of the nervous system, and the body, i.e., head, neck, thorax, and abdomen. Vagal nerve blocking (using high frequency electrical signals) and nerve stimulation (using low frequency electrical signals) have been found to affect afferent sensory fibers and messages to the brain related to food intake, energy metabolism, and glycemic control. These mechanisms can be used to control weight loss in humans, for example, by "mimicking" satiety signals to the brain indicating that the stomach is full of food and thus curb further eating. However, these methods are limited by the body's compensation responses that blunt physiological responses if nerves are over-stimulated by signals. Persistent stimulation may also cause tissue damage.

Solutions for selectively transmitting electrical stimulation to the vagal nerve on a set schedule have had their shortcomings because the complex circuitry required to elicit pre-scheduled electrical stimulation requires large amounts of battery power and cannot accurately predict the timing of users' food intake.

SUMMARY OF THE INVENTION

The present invention provides an implantable vagal nerve stimulator having a "passive" power generator that harvests energy from the stomach's movements to transform that kinetic energy to electrical energy eliminating the need for a battery. In this regard, the invention is self-powering to simply and automatically respond to stomach peristalsis. While sporadic stimulation to the vagal nerve would seem too infrequent to cause weight loss effects, electrical stimulation delivered at the optimal time (e.g., during food consumption) has been found to optimize the effects of vagal nerve stimulation, giving the user's brain a "full stomach" feeling before the user overeats.

In one embodiment, a triboelectric generator device is implanted onto the surface of a human stomach. The device is electrically connected through electrodes to anterior and posterior vagal nerves leading to the brain. When the stomach is in peristalsis (e.g., during food intake) the triboelectric generator device, containing triboelectric layers, contact and separate causing a small electrical voltage to form and current to be released to the vagal nerve. The electrical stimulation mimics signals to the brain sent via vagal afferent fibers that synapse in the nucleus tractus solitaries in the hindbrain so that the user thinks that the stomach is full and is satiated and will not consume any more food. The invention results in a self-powered energy generator that can be implanted within the abdomen and can convert mechanical energy of stomach peristalsis to electrical energy for auto-responsive stimulation to the vagus nerve.

The present invention provides a nerve stimulation device including a generator communicating with a stomach and adapted to convert mechanical energy harvested from a peristalsis of the stomach into electric pulses; and a first and second electrode electrically communicating the electric pulses from the generator to a vagal nerve.

It is thus a feature of at least one embodiment of the invention to decrease the amount of electrical stimulation to a patient by delivering electrical stimulation during stomach peristalsis only.

The nerve stimulation device may be comprised exclusively of passive electrical components incapable of controlling current by means of another electrical signal.

It is thus a feature of at least one embodiment of the invention to simplify the circuitry of the device.

The nerve stimulation device may operate using power only from the generator. The nerve stimulation device may operate without batteries.

It is thus a feature of at least one embodiment of the invention to eliminate the necessity of charging or replacing a battery powering the device.

The generator may include a first and second material movable with respect to each other with peristalsis of the stomach wherein the first and second material have divergent electron affinities. Movement of the first and second material may create a voltage across the first and second material.

It is thus a feature of at least one embodiment of the invention to provide responsive electrical stimulation delivery instead of electrical stimulation on a predetermined schedule.

The generator material may be comprised of two metal electrodes separated by a dielectric film. The dielectric film may be attached to one electrode and the other electrode may move with respect to the dielectric film. The generator material may be comprised of a copper (Cu) film and a polytetrafluoroethylene (PTFE) film with a back electrode attached to it.

It is thus a feature of at least one embodiment of the invention to utilize the movement of the stomach tissue and triboelectric effect to generate electrical charge.

The movement between the first and second material may be separation and abutment of plates. Alternatively, the movement between the first and second material may be a sliding motion.

The generator may be carried by a housing attachable to a surface of the stomach.

It is thus a feature of at least one embodiment of the invention to utilize the compression and expansion of the stomach tissue during peristalsis to effectuate movement between triboelectric materials.

The housing may be a compressible tube and the first and second material may be held within the compressible tube, where the first and second material are separated by an inner lumen of the tube extending along a longitudinal axis of the tube in a first state and the first and second material are in contact in a second state. The first and second electrode may be insulated wires.

It is thus a feature of at least one embodiment of the invention to provide a biocompatible device that can be implanted on the stomach with minimally invasive surgery.

The nerve stimulation device may have a switch preventing electrical communication between the vagal nerve and the generator. The electrical switch may be a reed switch.

It is thus a feature of at least one embodiment of the invention to provide flexible on-off control of electrical stimulation delivery.

The first and second electrode may be biodegradable such that the first and second electrode disintegrates harmlessly within the body over a certain amount of time.

It is thus a feature of at least one embodiment of the invention to provide deactivation of electrical stimulation delivery over time.

The nerve stimulation device may be a piezoelectric generator.

It is thus a feature of at least one embodiment of the invention to utilize the movement of the stomach tissue and piezoelectric effect to generate electrical charge.

The present invention also provides a method of vagal nerve stimulation device including the steps of: providing a nerve stimulation device having a generator communicating with a stomach and adapted to convert mechanical energy harvested from a peristalsis of the stomach into electrical energy, and a first and second electrode electrically communicating the electrical energy from the generator to a vagal nerve; implanting the nerve stimulation device on the stomach; and attaching the first and second electrode to the vagal nerve.

The method may further comprise the step of implanting multiple nerve stimulation devices on the surface of the stomach.

These particular objects and advantages may apply to only some embodiments falling within the claims and thus do not define the scope of the invention.

BRIEF DESCRIPTION OF THE DRAWINGS

FIG. 5 is a flow chart showing assembly of the triboelectric device; and

FIG. 6 is a flow chart showing operation of the triboelectric device to stimulate the vagus nerves for weight control.

DETAILED DESCRIPTION OF THE PREFERRED EMBODIMENT

Figure 1:
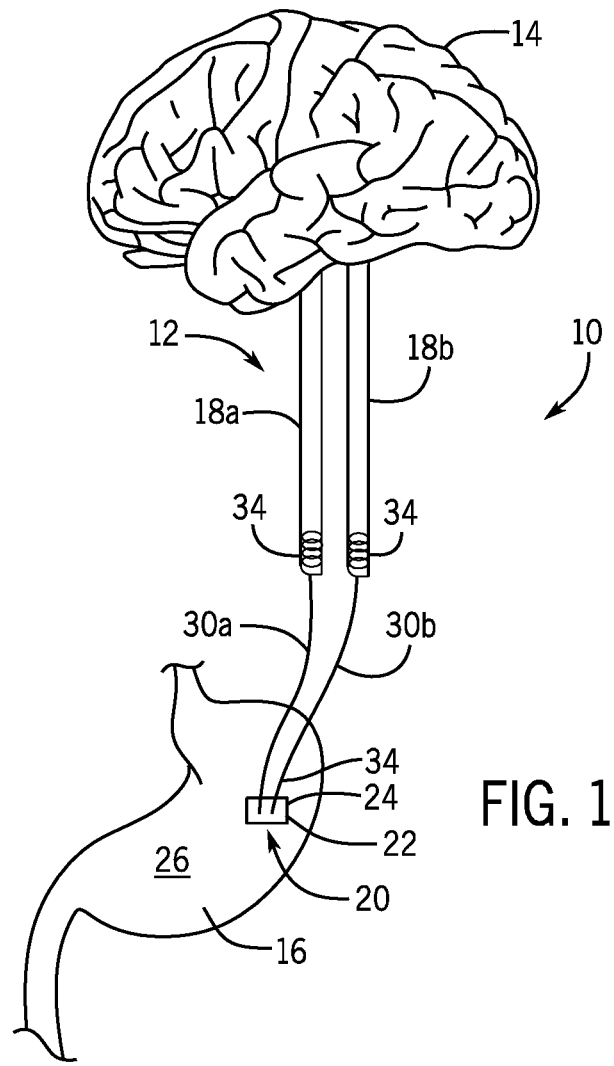
FIG. 1 is a schematic view of a device implanted on a human stomach and electrically connected to vagal nerves sending signals to the brain.

Referring now to FIG. 1, an electrical nerve stimulation system 10 may be used to stimulate vagus nerves 12 of a human patient. The vagus nerve 12 is the tenth cranial nerve emerging directly from the brain 14 and relaying information between the brain 14 and other parts of the body (i.e., head, neck, thorax, and abdomen). The vagus nerve 12 contains both afferent and efferent sensory fibers that modulate, regulate, and integrate gastrointestinal mechanisms of the stomach 16. Efferent sensory signals running from the brain 14 to the stomach 16 affect digestion, secretion of digestive enzymes, and gastrointestinal motility. For example, the vagus nerve 12 sends signals for regulating peristalsis (i.e., the contraction and relaxation) of the stomach muscles to drive food from the stomach 16 into the small intestines. Afferent sensory signals running from the stomach 16 to the brain 14 affect the human patient's perception of hunger, mood and stress levels, and fullness and inflammatory stress responses. For example, as food fills the stomach 16, satiety signals are sent through the vagus nerves 12 to the brain 14. The present invention utilizes the afferent sensory signal mechanism to send electrical charge through the vagus nerves 12 to "mimic" satiety signal sent through the vagus nerves 12 to the brain 14.

The electrical nerve stimulation system 10 may include an electrical stimulator 20 implanted in the human patient. The electrical stimulator 20 may include an outer housing 22 attached to the stomach 16 and supporting a generator 24 that converts mechanical energy produced by small-scale physical changes to the generator 24 into electricity. The outer housing 22 may be attached to an outermost layer or serosa 26 of the stomach 16 so that the generator 24 may harvest the movements of the stomach 16. For example, the generator 24 may use the expansion and contraction of the serosa 26 of the stomach 16 occurring during peristalsis to this kinetic energy to electrical energy that can then be used as an electrical stimulus, as further described below.

The electrical stimulator 20 may electrically communicate the electrical stimulus or charge to the vagus nerves 12 via one or more electrode wires 30, for example, a first electrode wire 30a and a second electrode wire 30b, extending between the electrical stimulator 20 and the vagus nerves 12. The electrode wires 30 may be insulated conducting wires, for example, copper wires insulated with polydimethylsiloxane (PDMS) to prevent charge from flowing to the surrounding tissue being dissipated in surrounding tissue or exposing the tissue to chemical reactions. The ends of the electrode wires 30 may have biocompatible leads 34, for example, gold wire leads, for connection to the vagus nerves 12. The electrode wires 30 may be approximately 15-25 mm or 20 mm in length and the biocompatible leads 34 may be approximately 10-20 mm or 15 mm in length.

The electrode wires 30 may interface with distal branches of the vagus nerve 12, namely, the first electrode wire 30a may communicate with an anterior vagal trunk 18a and the second electrode wire 30b may communicate with a posterior vagal trunk 18b, for example, by sticking the biocompatible leads 34 of the electrode wires 30 into the respective vagus nerves 12. The anterior vagal trunk 18a and posterior vagal trunk 18b are a part of the esophageal plexus, which extends from the human patient's esophagus to the stomach 16. The biocompatible leads 34 and/or electrode wires 30 may be wound or coiled around the vagus nerves 12 to secure the electrode wires 30 to the vagus nerves 12. The electrode wires 30 may also be sutured or otherwise adhered to the vagus nerves 12 to prevent dislodgment or disconnection of the biocompatible leads 34 from the vagus nerve 12. The electrode wires 30 and biocompatible leads 34 may deliver an electrical charge generated by the electrical stimulation device 20 to the vagus nerves 12 as further described below.

The generator 24 may be a power generator that converts mechanical or kinetic energy into electrical energy, for example, the generator 24 may be a triboelectric generator, a piezoelectric generator, or an electret capacitor with movable plates of the type known in the art. In this respect, the generator 24 may be any type of power generator that uses the movements of the stomach 16 during peristalsis to convert the mechanical or kinetic energy into electrical energy delivered to the vagus nerves 12 as an electrical charge. This is in contrast to stored chemical energy such as may be provided by a battery that must be recharged or reloaded over time.

Figure 2:
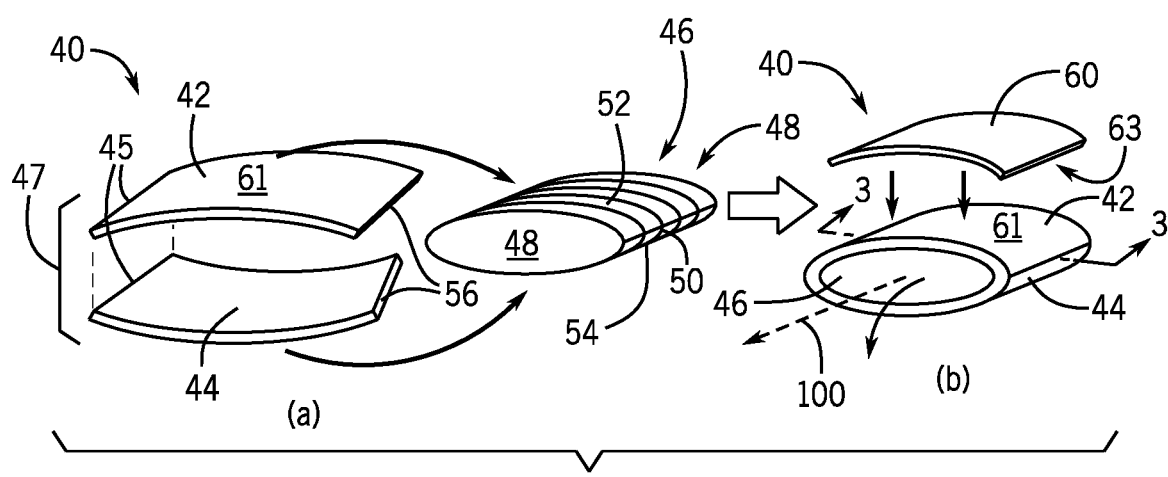
FIG. 2 is a perspective view of a triboelectric device of one embodiment of the present invention showing formation of a bottom copper (Cu) electrode and a top polytetrafluoroethylene (PTFE) film with a back copper (Cu) electrode attached to it.
Figure 3:
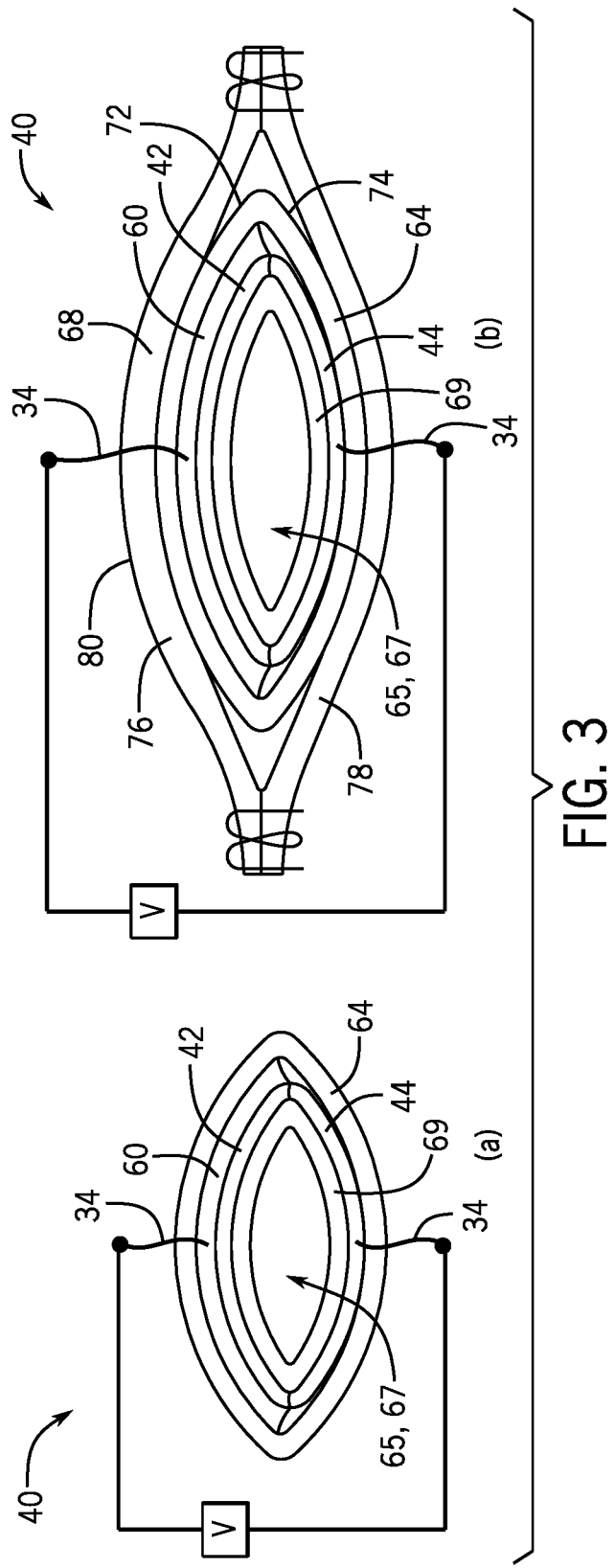
FIG. 3 is a cross-sectional view of the triboelectric device of FIG. 2 along line 3-3 the triboelectric device installed within a flexible plastic tubing and further covered by a packing layer for bonding to the stomach surface.

Referring now to FIGS. 2 and 3, in one embodiment of the present invention, the generator 24 is a triboelectric generator 40 that produces energy through movement of separation and abutment of plates. The triboelectric generator 40 may also be of the type to generate energy through lateral sliding of the plates or single electron modes. The triboelectric generator 40 may convert mechanical or kinetic energy into electrical energy by utilizing the "triboelectric effect" and "electrostatic induction" of plates of two different materials having opposite electron affinity, for example, copper and polytetrafluoroethylene (PTFE). In this example, PTFE attracts electrons from copper resulting in positive triboelectric charges on the copper side and negative triboelectric charges on the PTFE side. Due to the peristaltic movement of the serosa 26 of the stomach 16, there is a separation and contact of the two different materials causing a voltage between the two different materials to form, and thus, causing the back and forth flow of current between the two different materials as the materials separate and connect.

It is understood that various triboelectric materials may be used in the construction of the triboelectric generator 40 such that the two materials have opposite electron affinity relative to each other. For example materials that generally attract electrons include polyvinylchloride, polypropylene, polyethylene, polystyrene, polycarbonate, polyethylene terephthalate, and the like. Materials that generally attract a positive charge include glass, mica, polyamide (nylon 6,6), wool, aluminum, paper, steel, wood, amber, and the like.

Referring to FIG. 2a, the triboelectric generator 40 may be formed by initially processing a thin film 42 of dielectric material such as PTFE using reactive-ion etching to introduce nanostructures into the surface of the PTFE film 42 to enhance its electrical output. For example, 5 nm of gold may be first sputtered onto the PTFE film 42. Then, the PTFE film 42 may be treated in an inductively coupled plasma chamber of mixed etching gases, i.e., Ar, $O_2$, and $CF_4$, for approximately 30 seconds. The PTFE film 42 may be a rectangular film and be approximately 50 μm thick and between 0.5 to 0.8 cm in length and width.

An edge of the PTFE film 42 may be coupled to a metal material such as a copper film 44, at a binding edge 45. The PTFE film 42 and the copper film 44 may be bound to each other along the binding edge 45 through an adhesive or bonding method. The copper film 44 may be approximately the same size as the PTFE film 42, and thus may be rectangular film and be approximately 50 μm thick and between 0.5 to 0.8 cm in length and width. Corresponding of the PTFE film 42 and copper film 44 may be attached at the common binding edge 45 such that the PTFE film 42 and copper film 44 create larger rectangular film or sheet. The attachment of the PTFE film 42 and the copper film 44 may form a dual material sheet 47.

The dual material sheet 47 of PTFE film 42 and copper film 44 may be rolled onto a mold or template 46 to define a tubular geometry of the triboelectric layers. The template 46 may be a solid oval cylinder having oval bases 48 at opposed ends of a curved surface 50 extending along a longitudinal axis 100 corresponding with a length of the oval cylinder. The curved surface 50 may be striped to facilitate adhesion. The surface area of the curved surface 50 may be commensurate with the surface area of the dual material sheet 47 of PTFE film 42 and copper film 44. In this respect, the dual material sheet 47 of PTFE film 42 and copper film 44 may be wrapped around the outside of the curved surface 50 of the oval cylinder to substantially cover the curved surface 50. For example, the PTFE film 42 of the dual material sheet 47 may substantially cover an upper surface 52 of the template 46 and the copper film 44 may substantially cover a lower surface 54 of the template 46. After wrapping, the free ends 56 of the dual material sheet 47 opposite the binding edge 45 may be coupled or bonded in order to form a cylinder or tube wrapped around the template 46. Alternatively, the free ends 56 may be left uncoupled or bonded and instead may be held in place during the rolling process until secured by an outer jacket 64 as further described below.

Referring to FIG. 2b, once the PTFE film 42 and copper film 44 are wrapped around the template 46, an additional metal electrode such as a second copper film 60 may be attached to the backside of the PTFE film 42. The PTFE film 42 and the second copper film 60 may be bound to each other between an upper face 61 of the PTFE film 42 and a lower face 63 of the second copper film 60 through an adhesive or bonding method. In this respect, the upper PTFE film 42 and upper copper film 60 may form an upper triboelectric layer 62 of the triboelectric generator 40, and the lower copper film 44 may form a lower triboelectric layer 66 of the triboelectric generator 40. The template 46 may separate the upper triboelectric layer 62 and lower triboelectric layer 66.

The copper film 60 may define an upper electrode of the triboelectric generator 40 while the copper film 44 defines the lower electrode of the triboelectric generator 40. In this respect, the electrodes wires 30a, 30b may be coupled to the upper copper film 60 and lower copper film 44, respectively. The PTFE film 42 may serve as a dielectric material extending the upper and lower electrodes.

The template 46 may be removed from the upper and lower triboelectric layers 62, 66 to form a hollow cylinder or tube comprised of the upper and lower triboelectric layers 62, 66 forming a wall of the cylinder or tube and defining an inner lumen 67 extending along axis 100 through the tube and generally corresponding with the dimensions of the removed template 46.

Referring now to FIG. 3a, the upper and lower triboelectric layers 62, 66 may be packaged by a multilayer encapsulation that is both non-cytotoxic and biocompatible.

A center spacer 69 such as a one or more layers of polyimide film may be inserted between the upper triboelectric layer 62 and lower triboelectric layer 66 to help retain separation between the upper and lower triboelectric layers 62, 66. The center spacer 69 may be upper and lower arches coinciding with the shape of the upper and lower triboelectric layers 62, 66 and joined at their ends to form a biconvex lens shaped passage therebetween. The center spacer 69 may be a resilient material allowing the upper triboelectric layer 62 and lower triboelectric layer 66 to bend toward each other and contact each other, but then spring back to a relaxed separated position. The polyimide film may have a thickness of approximately 50 μm.

The upper and lower triboelectric layers 62, 66 may be inserted into an outer jacket 64 defined by a plastic tube having a hollow passage 65 corresponding with the lumen 67 of the upper and lower triboelectric layers 62, 66. The upper and lower triboelectric layers 62, 66 may have an outer dimension less than but close to an inner dimension of the outer jacket 64. In this respect the layered template 46 may be inserted into the outer jacket 64 with the upper and lower triboelectric layers 62, 66 pressed against the inner surface of the outer jacket 64 by slight friction and slight expansion of the upper and lower triboelectric layers 62, 66 within the outer jacket 64 to retain the relative positions of the upper and lower triboelectric layers 62, 66 within the outer jacket 64. The outer jacket 64 may retain the general positioning of the upper and lower triboelectric layers 62, 66, while still maintaining the lumen 67 between the upper and lower triboelectric layers 62, 66.

Referring now to FIG. 3b, a biocompatible packing layer 68 may be casted over the top surface 72 and bottom surface 74 of the outer jacket 64 to create a tissue contacting surface. The packing layer 68 may include upper 76 and lower 78 layers forming a rectangular sheath enclosing the outer jacket 64 so that only the biocompatible leads 34, or part of the biocompatible leads 34, remain exposed and extend from the packing layer 68. The packing layer 68 may be approximately 1 mm thick and have a length and width of approximately 1 cm. The packing layer 68 may have a surface area that is greater than the surface area of the outer jacket 64 so that the packing layer 68 may be attached to the serosa 26 of the stomach 16 without disturbing or puncturing the outer jacket 64. For example, the packing layer 68 may extend over the outer jacket 64 so that the packing layer 68 may be sutured to the serosa 26 of the stomach 16 for example at two opposed corners of the rectangular packing layer 68 and without disrupting the outer jacket 64 or its contents. The packing layer 68 may be a polydimethylsiloxane (PDMS) pre-polymer, for example, PDMS having a 15:1 weight ratio manufactured by Dow Corning, and cured at approximately 60° C. for two hours.

Further, a layer of rubber sealant 80 may be coated onto the outer packing layer 68 to provide extra surface flexibility when attached to the serosa 26 of the stomach 16. The rubber sealant layer 80 may be approximately 200 μm thick. The layer of rubber sealant 80 may be a product sold under the name EcoFlex manufactured by Smooth-On, Inc.

Figure 4:
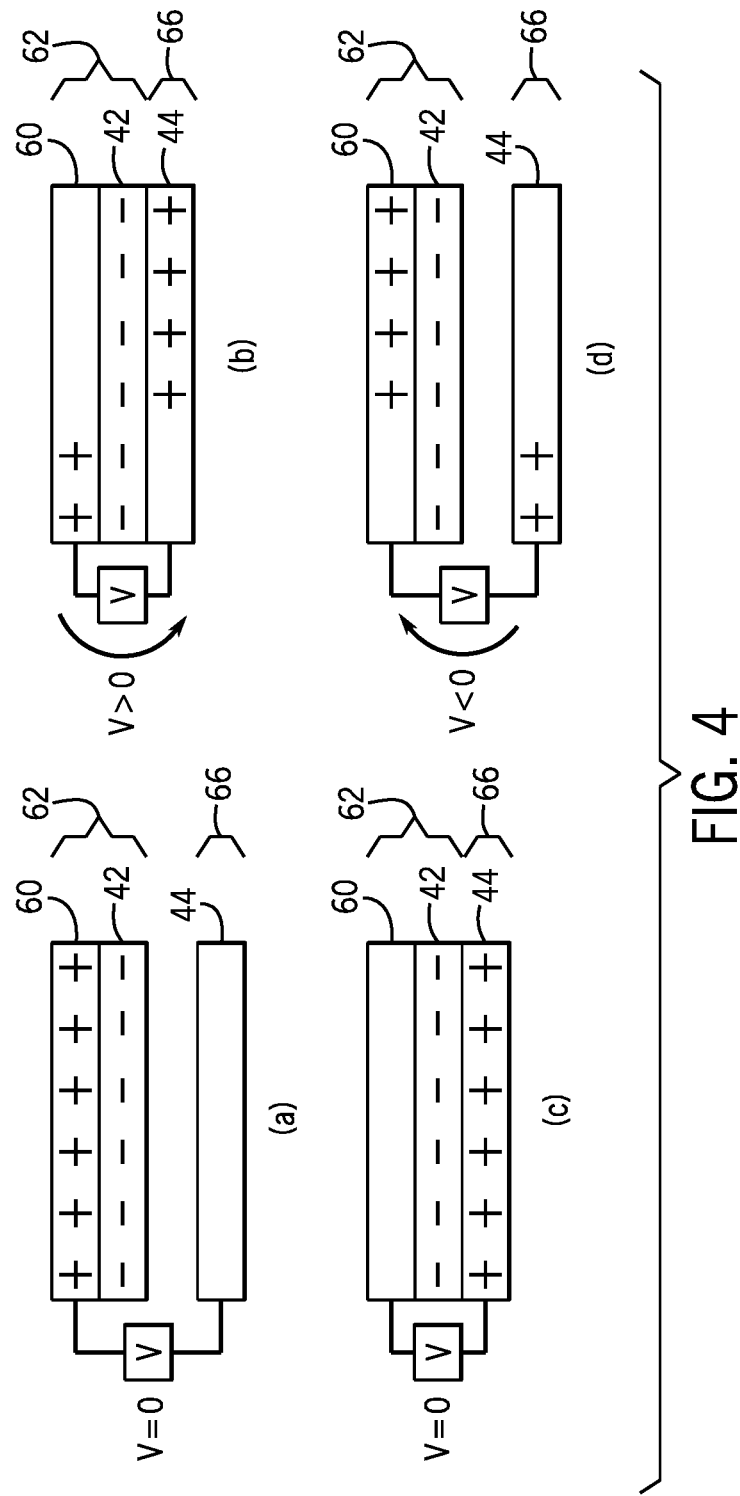
FIG. 4 is a schematic representation of the operation of the triboelectric device to produce biphasic electric current to the electrodes.

Referring now to FIG. 4, once the triboelectric generator 40 is attached to the serosa 26 of the stomach 16, operation of the triboelectric generator 40 to stimulate the vagus nerves 12 may occur automatically with natural peristaltic movement of the stomach 16 as described below. In this respect the triboelectric generator 40 does not need a battery or any active electrical components to produce an electric charge and is self-powered.

Referring to FIG. 4a, when the stomach is not in peristalsis, the human patient may be fasting or not consuming food. In this first "relaxed state," the stomach 16 walls are relaxed and not in peristalsis. In the relaxed state, the stomach 16 walls are fully contracted and the sutured edges of the outer jacket 64 of the triboelectric generator 40 are brought closer together such that the upper triboelectric layer 62 and lower triboelectric layer 66 are separated, similar to squeezing open a squeeze coin purse. When the upper and lower triboelectric layers 62, 66 are separated, the charges are balanced and there is no voltage between the upper and lower triboelectric layers 62, 66 (V=0). There is no current flow through the electrode wires 30.

Referring to FIGS. 4b-4d, when the stomach is in peristalsis, the human patient may be feeding or consuming food. In this second "peristalsis state", the stomach 16 may be filling with food and the stomach walls are in peristalsis, exhibiting regular peristaltic contraction waves. The contraction waves have a typical propagation velocity of about 1.5 mm/s and a frequency of about three cycles/min. During the second peristalsis state the cycle of contraction and distention repeat until the peristalsis of the stomach 16 stops to resume to first relaxed state.

Referring to FIG. 4b, during peristaltic "distention", the stomach 16 walls are expanded and the sutured edges of the outer jacket 64 of the triboelectric generator 40 are stretched apart such that the upper triboelectric layer 62 and lower triboelectric layer 66 are in contact, similar to releasing and closing a squeeze coin purse. Since the upper PTFE film 42 has a high electron affinity while the lower copper film 60 has a low electron affinity, when the layers contact, positive triboelectric charges want to form on the lower copper film 60 and negative triboelectric charges want to form on the upper PTFE film 42. In order for the positive triboelectric charges to form on the lower copper film 60, positive charge flows from the upper copper film 60 down to the lower copper film 44 to produce a positive voltage between the upper and lower triboelectric layers 62, 66 (V>0). The positive charge flowing from the upper copper film 60 down to the lower copper film 44 through the electrode wires 30 stimulate the vagus nerves 12.

Referring to FIG. 4c, the positive charge flows from the upper copper film 60 to the lower copper film 44 until the positive triboelectric charges on the lower copper film 44 and the negative triboelectric charges on the upper PTFE film 42 are balanced. At this point, there is no voltage between the upper and lower triboelectric layers 62, 66 (V=0) and there is no charge flowing through the electrode wires 30 to further stimulate the vagus nerves 12.

Referring to FIG. 4d, distention of the stomach 16 is followed by peristaltic "contraction" where the stomach walls tighten or shrink and the edges of the outer jacket 64 are brought closer together such that the upper triboelectric layer 62 and lower triboelectric layer 66 are separated again, similar to squeezing open a squeeze coin purse. As the upper triboelectric layer 62 and the lower triboelectric layer 66 separate, the positive charge stored in the lower copper film 44 is driven back up to the upper copper film 60 to produce a negative voltage between the upper and lower triboelectric layers 62, 66 (V<0). The positive charge flowing in the opposite direction from the lower copper film 44 to the upper copper film 60 through the electrode wires 30 further stimulates the vagus nerves 12.

Referring again to FIG. 4a, the positive charge flows from the lower copper film 44 to the upper copper film 60 until the positive triboelectric charges on the upper copper film 60 and the upper PTFE film 42 are balanced. Therefore, there is no voltage between the upper and lower triboelectric layers 62, 66 (V=0) and there is no charge flowing through the electrode wires 30 to further stimulate the vagus nerves 12.

The cycle of stomach contraction and distention shown in FIGS. 4a-4d repeat during peristalsis of the second peristalsis state to produce biphasic pulses of current flow through the vagus nerves 12. It has been found that the biphasic pulses of current flow repeatedly stimulates the vagus nerves 12 to mimic satiety signals to the brain 14 and to give the human patient a "full stomach" feeling and prevent overeating.

The voltage exhibited during the cycle of stomach contraction and distention may vary from 0.05V to as much as 5V. The voltage is directly related to the impedance of the nerve tissue, about 0.3 MΩ. Higher voltage outputs are recorded at higher stimulation frequencies. The amount of power generated by the triboelectric generator 40 may be about 40 μW at an external load of 20 MΩ.

In order to set a threshold amount of stomach 16 movement needed before electrical stimulation is delivered to the vagus nerves 12, the triboelectric generator 40 may be pre-strained. In this respect, the triboelectric generator 40 will not provide electrical stimulation with small peristaltic movements of the stomach occurring through, for example, normal stretching of the abdomen or after smaller intake of food such as a small snack. Thus electrical stimulation will only occur during larger peristaltic movements of the stomach occurring through, for example, larger consumption of food that is consistent with overeating. For example, a spring or arched material may be placed between the upper triboelectric layer 62 and lower triboelectric layer 66, or the center spacer 69 between the upper triboelectric layer 62 and lower triboelectric layer 66 may be selected with a higher stiffness, so that a greater force is required before the upper triboelectric layer 62 and lower triboelectric layer 66 will contact and separate.

In the operation of the above-described electrical nerve stimulation system 10, the electrical stimulator 20 may be used to stimulate the vagus nerves 12 of a human patient in order to mimic satiety signals send through the vagus nerves 12 to the brain 14.

Referring to FIG. 5, in one embodiment of the present invention, the electrical stimulator 20 includes a generator 24 which may be a triboelectric generator 40 formed according to the assembly shown in FIGS. 2 and 3.

First, an upper PTFE film 42 and lower copper film 44 are rolled onto an oval cylindrical template 46, as represented by process step 112 (FIG. 2*a*). Next, a second, upper copper film 60 is bonded to the upper PTFE film 42, as represented by process step 114 (FIG. 2*b*). Electrode wires 30 may be attached to the upper cooper film 60 and the lower copper film 44, as represented by process step 116 (FIG. 2*b*).

Next, the template 46 may be removed from the upper and lower triboelectric layers 62, 66, as represented by process step 118 (FIG. 2*b*). In its place a center spacer 69 may be inserted between the upper triboelectric layer 62 and lower triboelectric layer 66 to retain the lumen 67 between the upper and lower triboelectric layer 62, 66 (FIG. 3*a*), as represented by process step 120.

Next, the rolled upper and lower triboelectric layers 62 may be inserted into the outer jacket 64 to retain the tubular geometry of the upper and lower triboelectric layers 62, 66, as represented by process step 122 (FIG. 3*a*).

Lastly, the outer packing layer 68 may be casted over the outer jacket 64 to encapsulate the outer jacket 64 and to allow the packing layer 68 to be sutured to the serosa 26, as represented by process step 124 (FIG. 3*b*). Optionally a layer of rubber sealant 80 may also be coated over the outer packing layer 68.

Referring to FIG. 6, implantation of the triboelectric generator 40 may include attaching the outer packing layer 68 to the stomach 16, for example, suturing the outer packing layer 68 to the serosa 26 of the stomach 16 toward an anterior portion of the stomach 16, so that the triboelectric generator 40 may detect and harvest the movements of the stomach serosa 26 or outer stomach tissue during stomach peristalsis, as represented by process step 150. The outer packing layer 68 may also be attached to the inner muscular walls of the stomach which may be more sensitive to movement, such as inner or outer surfaces of the muscularis externa layer.

Electrical wires 30*a*, 30*b* of the triboelectric generator 40 may be attached to the anterior vagal trunk 18*a* and posterior vagal trunk 18*b* of the vagus nerves 12 proximate the gastro-oesophageal junction at the lower part of the esophagus that connects to the stomach 16, as represented by process step 152. The anterior vagal trunk 18*a* and the posterior vagal trunk 18*b* may be approximately 4-8 mm or 6 mm apart. This electrical wire 30*a*, 30*b* attachment may provide focused stimulation to the small unmyelinated C fibers and avoid stimulating fibers that join the truck from the heart and lungs.

The stomach will undergo cycles between the first relaxed state, in which no electrical stimulation is delivered, as represented by block 154, and the second peristalsis state, when electrical stimulation is repeatedly delivered for a period of time responsive to peristalsis, as represented by block 156 and process step 158. During electrical stimulation, electrical stimulation to the vagus nerves 12 will send signals to the brain 14 telling the human patient that the stomach 16 is full to curb the patient's eating patterns.

The cycle between the first relaxed state 154 and second peristalsis state 156 will repeat over time to provide long-term electrical stimulation responsive to peristalsis of the stomach 16.

In order to control the amount of electrical stimulation sent to the brain 14, more than one generator 24 may be implanted on the stomach 16 and separately controlled in order to activate or deactivate a desired number of generators 24. For example, more generators 24 may be activated in order to elicit more electrical stimulation while less generators 24 may be activated in order to elicit less electrical stimulation.

Ideally, the present invention provides a simple passive electrical device that does not require an external source to operate. However, additional active or passive electrical devices may be implemented into the circuitry of the electrical stimulator 20. For example, on-off circuitry may be incorporated to disable and/or enable the flow of current through the electrode wires 30 such as a switch. The switch may be a manually operated switch or a reed switch responding to the proximity of a nearby magnet to open or close electrical contacts when a magnetic field is present.

All or part of the generator 24, including the electrode wires 30 may be biodegradable so that the wires disintegrate harmlessly within the body over a certain amount of time, for example in less than three years. In this regard, the conductors may use metallic glasses based on magnesium zinc and calcium or thin aluminum conductors covered with biodegradable insulator such as silk. The PTFE film 42 may make use of the material such as alginate film and the other materials described in "An alginate film-based degradable triboelectric generator", Yokunk Pang et al. RSC Adv., 2018, 8, 6719, hereby incorporated by reference.

The term "passive electrical device" refers to components incapable of controlling current by means of another electrical signal. For example, resistors, capacitors, inductors, and transformers, are passive electrical devices.

The term "active electrical device" refers to a circuit component, which requires external source to operate. For example, diodes, transistors, silicon controlled rectifiers and thyristors are active electrical devices.

A "full stomach" refers to the absence of hunger feelings or the sensation of feeling full. Normally, stretch receptors work to inhibit appetite upon distention of the stomach by sending signals along the vagus nerve afferent pathway and inhibiting the hunger center. The delivery of these signals gives the person a "full stomach" feeling.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a microprocessor" and "a processor" or "the microprocessor" and "the processor," can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

What we claim is:

1. A nerve stimulation device comprising:
a generator providing a pair of triboelectric materials and a first and second attachment point adapted to attach to two different locations on a stomach so that peristalsis of the stomach provides relative movement between the attachment points and corresponding relative movement between the pair of triboelectric materials to convert mechanical energy harvested during a peristalsis of the stomach into electrical energy; and
a first and second electrode adapted to electrically communicate the electrical energy from the generator to a vagal nerve
wherein the pair of triboelectric materials are connected to the first and second electrode, respectively, and have divergent electron affinities operable to produce an operative amount of electrical energy to stimulate the vagal nerve by movably contacting each other.

2. The device of claim 1 wherein the nerve stimulation device is comprised exclusively of passive electrical components incapable of controlling current by means of another electrical signal.

3. The device of claim 1 wherein the nerve stimulation device operates using power only from the generator.

4. The device of claim 1 wherein the nerve stimulation device operates without batteries.

5. The device of claim 1 wherein movement of the pair of triboelectric materials creates a voltage across the pair of triboelectric materials.

6. The device of claim 1 wherein the pair of triboelectric materials of the generator is comprised of two metal layer electrodes separated by a dielectric film.

7. The device of claim 6 wherein the dielectric film is attached to one layer electrode and the other layer electrode may move with respect to the dielectric film.

8. The device of claim 7 wherein the generator material is comprised of a copper (Cu) film and a polytetrafluoroethylene (PTFE) film with a back layer electrode attached to it.

9. The device of claim 1 wherein movement between the pair of triboelectric materials is separation and abutment of plates.

10. The device of claim 1 wherein movement between the pair of triboelectric materials is a sliding motion.

11. The device of claim 1 wherein the generator is carried by a housing attachable to a surface of the stomach.

12. The device of claim 1 wherein the nerve stimulation device has a switch preventing electrical communication between the vagal nerve and the generator.

13. The device of claim 12 wherein the electrical switch is a reed switch.

14. The device of claim 1 wherein the first and second electrode are biodegradable such that the first and second electrode disintegrate harmlessly within a body over a certain amount of time.

15. The device of claim 1 wherein the first and second electrode are insulated copper wires.

16. The device of claim 1 wherein the first and second attachment points are at opposite ends of the generator.

17. A nerve stimulation device comprising:
a generator providing a pair of triboelectric materials and a first and second attachment point adapted to attach to two different locations on a stomach so that peristalsis of the stomach provides relative movement between the attachment points and corresponding relative movement between the pair of triboelectric materials to convert mechanical energy harvested during a peristalsis of the stomach into electrical energy; and
a first and second electrode electrically communicating the electrical energy from the generator to a vagal nerve;
wherein the generator is carried by a housing attachable to a surface of the stomach;
wherein the housing is a compressible tube and the pair of triboelectric materials are held within the compressible tube, wherein the pair of triboelectric materials are separated by an inner lumen of the tube extending along a longitudinal axis of the tube in a first state and the pair of triboelectric materials are in contact in a second state.

18. A method of vagal nerve stimulation device comprising:
providing a nerve stimulation device having a generator providing a pair of triboelectric materials and a first and second attachment point adapted to attach to two different locations on a stomach so that peristalsis of the stomach provides relative movement between the attachment points and corresponding relative movement between the pair of triboelectric materials to convert mechanical energy harvested during a peristalsis of the stomach into electrical energy, and a first and second electrode electrically communicating the electrical energy from the generator to a vagal nerve
wherein the pair of triboelectric materials are connected to the first and second electrode, respectively, and have divergent electron affinities operable to produce an operative amount of electrical energy to stimulate the vagal nerve by movably contacting each other;
implanting the nerve stimulation device on the stomach; and
attaching the first and second electrode to the vagal nerve.

19. The method of claim 18 further comprising the step of implanting multiple nerve stimulation devices on a surface of the stomach.

20. The method of claim 18 further comprising the step of suturing the generator at opposite ends at the first and second attachment points to the two different locations on the stomach.

* * * * *